(12) United States Patent
Rickett et al.

(10) Patent No.: US 12,131,808 B2
(45) Date of Patent: Oct. 29, 2024

(54) MASSIVELY PARALLEL PROCESSING DATABASE FOR SEQUENCE AND GRAPH DATA STRUCTURES APPLIED TO RAPID-RESPONSE DRUG REPURPOSING

(71) Applicant: HEWLETT PACKARD ENTERPRISE DEVELOPMENT LP, Houston, TX (US)

(72) Inventors: Christopher Douglas Rickett, Houston, TX (US); Kristyn J. Maschhoff, Seattle, WA (US); Sreenivas Rangan Sukumar, Seattle, WA (US)

(73) Assignee: Hewlett Packard Enterprise Development LP, Spring, TX (US)

( * ) Notice: Subject to any disclaimer, the term of this patent is extended or adjusted under 35 U.S.C. 154(b) by 54 days.

(21) Appl. No.: 17/118,520

(22) Filed: Dec. 10, 2020

(65) Prior Publication Data
US 2022/0189585 A1    Jun. 16, 2022

(51) Int. Cl.
G16B 50/00      (2019.01)
G06F 16/2457    (2019.01)
G06F 16/901     (2019.01)
G16B 30/00      (2019.01)

(52) U.S. Cl.
CPC ....... *G16B 50/00* (2019.02); *G06F 16/24578* (2019.01); *G06F 16/9024* (2019.01); *G16B 30/00* (2019.02)

(58) Field of Classification Search
None
See application file for complete search history.

(56) References Cited

U.S. PATENT DOCUMENTS 11,037,684 B2 *   6/2021  Hu ..................... G16H 50/50
2004/0204861 A1 * 10/2004  Benner ................. G16B 10/00
                                                    702/19

(Continued)

FOREIGN PATENT DOCUMENTS

WO    WO-2020070485 A1 *  4/2020

OTHER PUBLICATIONS

Chen et al., "Chem2Bio2PDF:a Semantic Framework for Linking and Data Mining Chemogenomic and Systems Chemical Biology Data", BioMed Central Ltd., 2010, 13 pages.

(Continued)

*Primary Examiner* — Alex Gofman
*Assistant Examiner* — Umar Mian
(74) *Attorney, Agent, or Firm* — Sheppard Mullin Richter & Hampton LLP

(57) ABSTRACT

Systems and methods disclosed herein may include a parallel-processing graph-database solution for protein-sequence analytics to determine a viable therapeutic for a given condition, and may include: determining a protein sequence for the given condition; using sequence database to compare a query sequence of the sequence of the given condition with sequences of other known proteins in the sequence database using the sequence database to determine a similarity of the query sequence with sequences of the other known proteins in the sequence database based on the comparison; and querying a graph database based on the similarity of sequences to identify potential therapeutics that could be have an inhibitory effect on the given condition.

20 Claims, 6 Drawing Sheets

(56) References Cited

U.S. PATENT DOCUMENTS

| | | | | |
|---|---|---|---|---|
| 2005/0154535 A1* | 7/2005 | Sun | ............ | G16B 5/00 |
| | | | | 702/19 |
| 2006/0036368 A1* | 2/2006 | Chen | ............ | G16B 5/20 |
| | | | | 702/19 |
| 2008/0082359 A1* | 4/2008 | Jung | ............ | G16B 20/00 |
| | | | | 705/2 |
| 2008/0086274 A1* | 4/2008 | Chamberlain | ......... | G16B 30/00 |
| | | | | 702/19 |
| 2016/0171173 A1* | 6/2016 | Xie | ............ | G16B 15/30 |
| | | | | 705/2 |
| 2017/0098032 A1* | 4/2017 | Desai | ............ | G16B 50/00 |
| 2017/0270245 A1* | 9/2017 | van Rooyen | ......... | G16B 20/10 |
| 2018/0121601 A1* | 5/2018 | Hahm | ............ | G16B 30/10 |
| 2019/0010533 A1* | 1/2019 | Wong | ............ | G16B 20/00 |
| 2019/0243946 A1* | 8/2019 | Postrel | ............ | C40B 30/00 |

OTHER PUBLICATIONS

Deng et al., "PhID: An Open-Access Integrated Pharmacology Interactions Database for Drugs, Targets, Diseases, Genes, Side-Effects, and Pathways", American Chemical Society, Sep. 14, 2017, pp. 2395-2400.
Kotlyar et al., "Network-based characterization of drug-regulated genes, drug targets, and toxicity", Elsevier Inc., 2012, pp. 499-507.
Sobhy, Haitham, "A bioinformatics pipeline to search functional motifs within whole-proteome data: a case study of poxviruses", Springer, 2017, 7 pages.

* cited by examiner

```
PREFIX arq: <http://jena-hplhp.com/ARQ/function#>
PREFIX rdf: <http://www.w3.org/1999/02/22-rdf-syntax-ns#>
PREFIX core: <http://purl.uniprot.org/core/>
PREFIX up: <http://purl.uniprot.org/core/> select ?protB ?name ?mnem ?sim
where {
# Look up the info for our sars2 spike protein
?protein a core: Protein .
?protein core: mnemonic 'SPIKE_SARS2'
?protein core: sequence ?isoform .
?isoform rdf: value ?seq .

# Look up all other proteins with sequence Info
?protB a core: Protein.
?protB core: sequence ?isoformB.
?IsoformB rdf: value ?seqB.
?protB core: mnemonic ?mnem
?protB up: recommendedName ?recommended.
?recommended up:fullName ?name.

# Compare the sars2 spike to each protein to get a sim value
bind(arq:user_func(?seq, ?seqB) as ?sim)
filter(?sim >0.2)
}
# List the proteins with the highest sim score first
order by desc(?sim)
```

Fig. 4

MASSIVELY PARALLEL PROCESSING DATABASE FOR SEQUENCE AND GRAPH DATA STRUCTURES APPLIED TO RAPID-RESPONSE DRUG REPURPOSING

DESCRIPTION OF RELATED ART

This disclosure relates generally to systems and methods for drug repurposing, and more particularly, some embodiments relate to a massively parallel graph database processes multi-modal data represented in the form of knowledge graphs and accelerates domain-specific functions to conduct protein similarity analysis to generate drug hypotheses.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIG. 4 illustrates an example of a sample query that can be used to perform protein sequence analytics.

Figure 1:
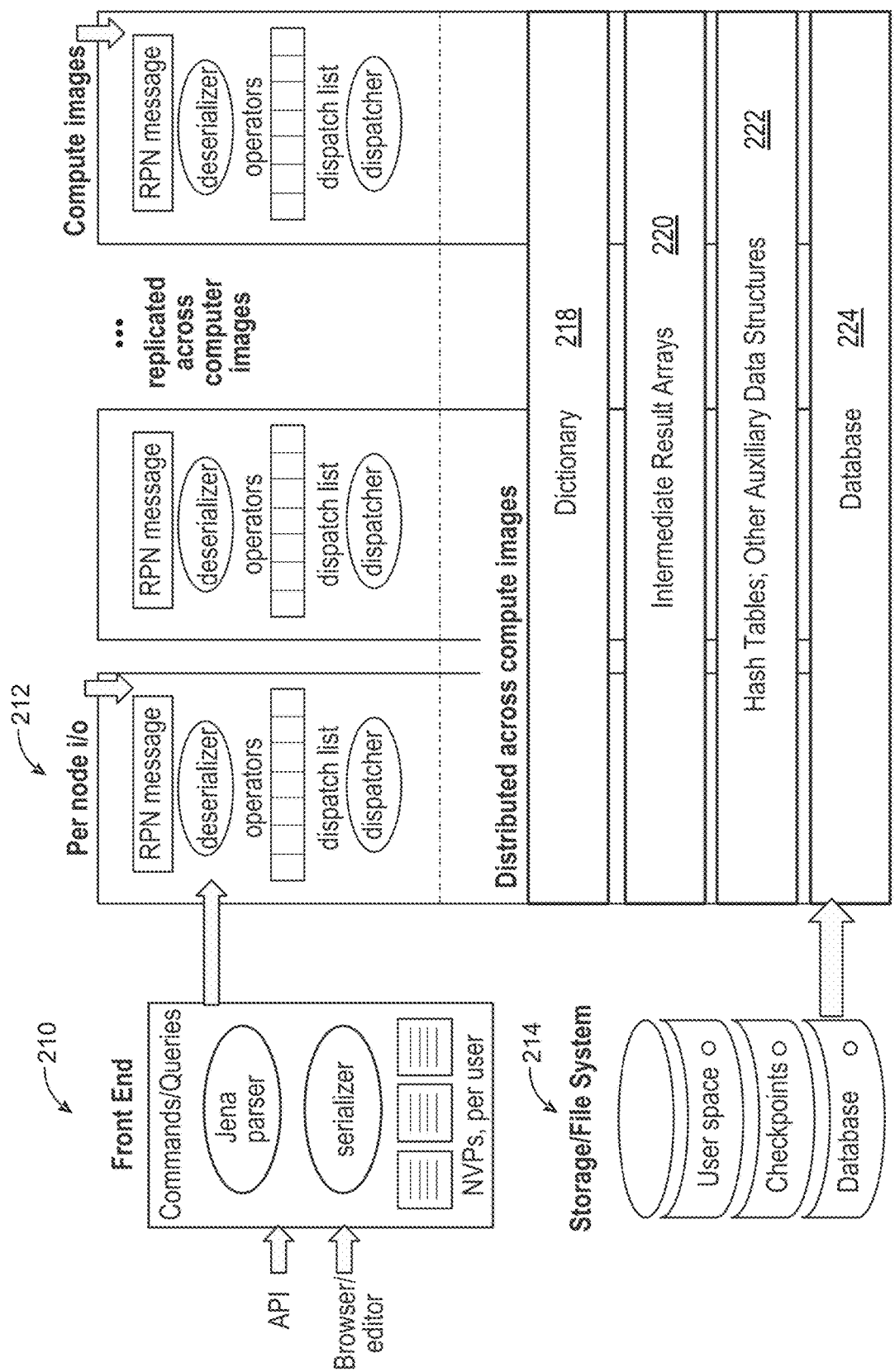
FIG. 1 illustrates an example graph engine in accordance with various embodiments.

The figures are not exhaustive and do not limit the present disclosure to the precise form disclosed.

DETAILED DESCRIPTION

Amidst the pandemic caused by the novel coronavirus, drug repurposing—the investigation of existing drugs for new therapeutic purposes—emerged as a first ray of hope toward the discovery of a medical cure. Drug repurposing, however is not limited to the coronavirus and may be used to identify therapeutics/drugs for any of a multitude of different conditions. A drug repurposing pipeline involves understanding the protein structures of the disease-causing organism, interpreting the interactions of the organism's protein structures with the human body, mining through properties of potential drug molecules, connecting the dots across curated literature to explain the mechanism-of-action, searching for evidence in assay data and analyzing for potential safety and efficacy using data from prior trials, and more. Conventionally, this process is done manually and takes several months.

The cumbersome nature of the problem is attributed to the time required for a life-sciences researcher to: (a) understand the disease-causing organism by matching and comparing protein sequences to previously known or studied disease-causing organisms (over 4 million sequences), (b) handle and process multi-modal Big data (protein sequences, proteomic interactions, bio-chemical pathways, structured data from past clinical trials etc.), (c) integrate and search for patterns connecting across the multiple multi-modal multi-terabyte datasets, (d) install, configure and run a plethora of tools (genetics, proteomics, molecular dynamics, data science etc.) to generate insights, and finally (e) verify and validate the scientific rigor for pharmacological interpretation. Embodiments of the systems and methods disclosed herein go beyond merely automating the conventional process and provide new technologies and techniques for implementing a repurposing pipeline. Embodiments may use a massively parallel-processing graph database technology to provide a more rapid response to accelerate the drug repurposing pipeline amidst a pandemic. This represents a massive improvement to current technology used to identify candidates for drug repurchasing/repositioning for known and novel diseases including, for example, new flu strains, coronaviruses, genetic rare diseases, etc. with protein-sequence analytics.

Embodiments relate to the application of a massively parallel-processing graph database for rapid-response drug repurposing. Implementations may use a scalable graph database configured to host a knowledge graph of medically relevant facts integrated from multiple knowledge sources and also act as a computational engine capable of in-database protein sequence analytics. Embodiments may be configured to use graph databases for multimodal drug repurposing based on processing sequences of a subject virus or other condition, identifying other known viruses/conditions with similar or matching sequences and querying properties of compounds and therapeutics that interact with those known viruses/conditions.

Embodiments may provide a massively parallel graph database that (a) stores, handles, hosts and processes multi-modal data represented in the form of knowledge graphs, (b) provides interactive query and semantic-traversal capabilities for data-driven discovery, (c) accelerates domain-specific functions such as Smith-Waterman algorithm to conduct protein similarity analysis, vertex-centric and whole-graph algorithms such as PageRank for graph-theoretic connectivity and relevance analysis, and (d) runs/executes a workflow of queries across multiple datasets to generate drug hypotheses in the order of seconds as opposed to months. Embodiments implement an integrated knowledge graph of multiple multi-modal life-science databases, conduct protein-sequence matching in parallel and provide a novel rapid drug-repurposing methodology that is able to query across 4+ million proteins, 155+ billion facts while handling approximately 30 terabytes of data.

Some applications implement a generalizable Big Data platform to other biomedical discovery problems beyond the COVID-19 pandemic, allowing: (a) A scalable graph database that offers order-of-magnitude computational speed-up and interactivity required for knowledge traversal and discovery, (b) An integrated life-sciences knowledge graph that captures the open-science universe of available biomedical facts, (c) hypotheses of potential drug candidates for the ongoing pandemic, (d) reproducible code and results for future studies on the universe of biomedical facts (on viruses, proteins, drugs, bio-chemical pathways) as opposed to the state-of-the-practice limited to disease-specific knowledge graphs.

Embodiments may be implemented using a Cray Graph Engine or other like engine. The Cray Graph Engine (CGE) is an in-memory semantic graph database designed to scale to hundreds of nodes and tens of thousands of processes on the Cray XC supercomputer to support interactive querying of large data sets (~100s of terabytes). The CGE ingests datasets of N-Triples/N-Quads based on the standardized Resource Description Framework (RDF) format and enables queries using the SPARQL query language. RDF data is expressed as a labeled, directed graph with the "quad" consisting of four fields: subject, predicate, object and graph. A triple is simply a quad that is stored in the "default graph". For example, the following is a simplified version of an example RDF triple from the Uniprot COVID-19 data that could be loaded into the CGE:

<urn:P0DTC2> <urn:mnemonic> "SPIKE_SARS2".

A graph as a data structure may include a network of possible connections. Vertices or nodes generally refer to entities (data, people, businesses, etc.) and connections between entities are edges. The graph database can be used to identify entities connected to other entities. Generally, local processing can be used to process small amounts of data around a node. However, other tasks may involve evaluating edges/connections on a more holistic basis (e.g., in a whole graph analysis). A semantic graph may include a collection of such triples with subjects and objects representing vertices and predicates representing edges between the vertices. Semantic graph databases differ from relational databases in that the underlying data structure is a graph, rather than a structured set of tables. The graph structure makes semantic databases ideal for analyzing multi-modal unstructured and structured data that is loosely connected or is schema-less—as is the case with social network interactions or interactions between proteins and genes in living organisms.

In various embodiments, the CGE may include two main components: the dictionary and the query engine. The dictionary is responsible for building the database, which is the process of ingesting raw N-Triples/N-Quads files from a high performance Lustre file system and converting them to the internal representation used by CGE. The dictionary stores the unique RDF strings from the N-Triples/N-Quads and provides a mapping between the unique strings and the integer identifiers used for the quads internally by the query engine. Much of the dictionary build time may be dominated by the Lustre I/O time.

The CGE query engine processes SPARQL queries and SPARUL update requests, provides a number of built-in graph algorithms (such as, for example, measures of centrality, PageRank, connectivity analysis) that can be applied to query data and returns results to the user. The core work performed by the query engine may include matching the basic graph pattern in the SPARQL queries as well as supporting operations on the query results, such as FILTER and ORDER, that allows users to remove and sort solutions, respectively.

Embodiments may be implemented that port CGE to improve the performance and scalability on supercomputer products with general-purpose processors using a high-performance interconnect. Multiple features are added above and beyond a conventional CGE to specifically support rapid response drug repurposing.

FIG. 1 illustrates an example graph engine in accordance with various embodiments. This example includes a front end 210, and a plurality of resources replicated across multiple computer images 212. These resources can include, for example, a deserializer, operators and a dispatcher as shown in compute images 212. The example graph engine can also include a dictionary 218, intermediate result to raise 220, hash tables and other exhilarating data structures 222 and a database 224. A storage file system 214 can be used to accommodate database 224 as well as user spaces, checkpoints and other data.

Front end 210 provides interface by which a user can interact with the graph engine such as, for example, by submitting queries and receiving results back from the queries. On the back inside, the graph engine runs on hardware they can be built on top of a partitioned global address space which may allow the system to treat independent processes and images as their own entity, but you can subdivide data and share data across the images using a communication library. The graph engine may be configured to run tens or hundreds of thousands of images in a coordinated manner, in which all can run independently on their own subset and the later synchronized when needed for results using the library.

Figure 2:
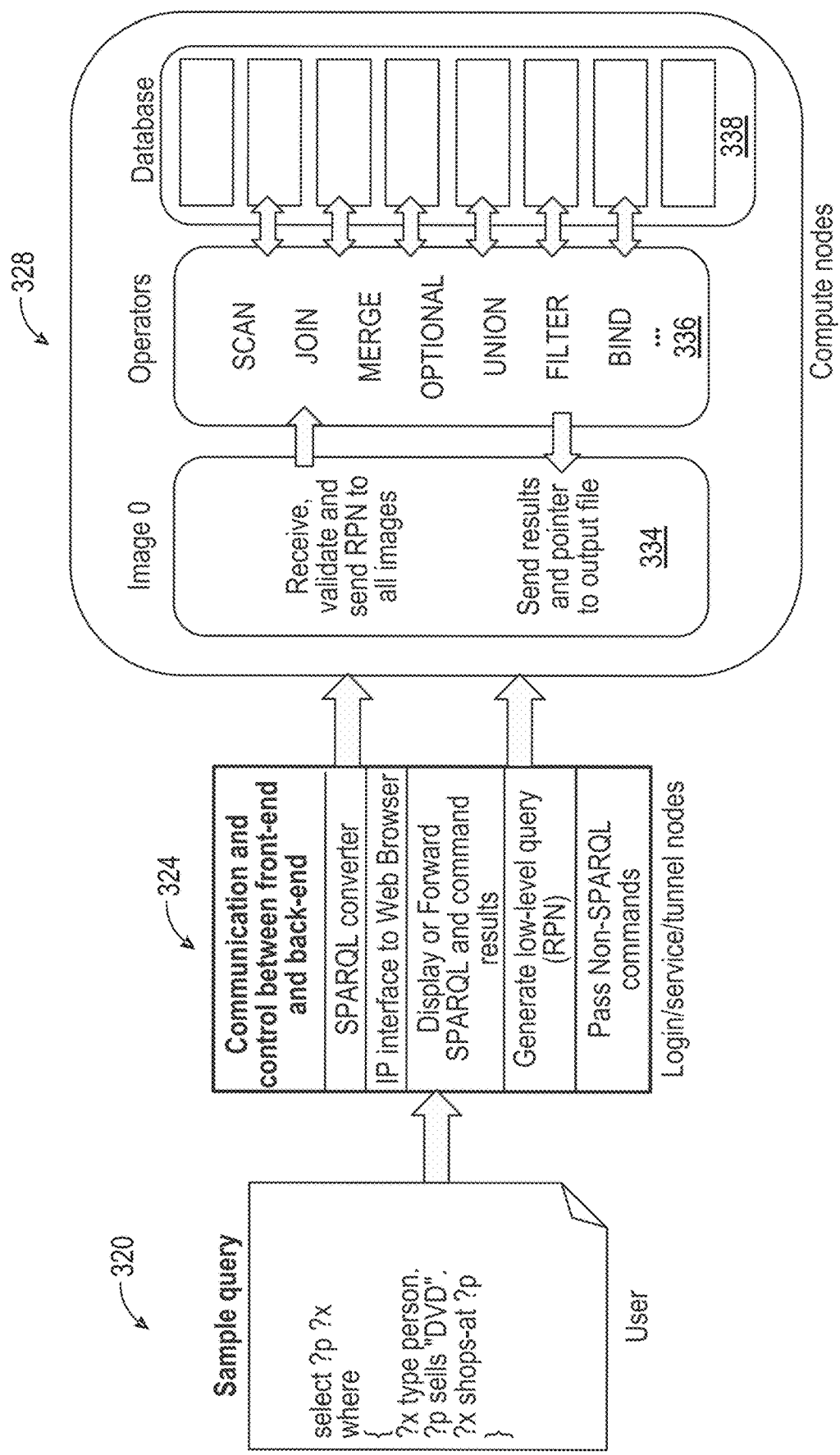
FIG. 2 illustrates an example of graph engine query execution in accordance with various embodiments.

FIG. 2 illustrates an example of graph engine query execution in accordance with various embodiments. Referring now to FIG. 2, an example query 320 may be submitted by a user. A communication interface 324 can provide communication and control between the front end (e.g., front end 210) and the back end compute nodes. In this example, the communication interface can include elements such as a SPARQL Protocol and RDF Query Language (SPARQL) converter, and IP interface to a web browser, a service to display or forward the SPARQL and command results, a service to generate low-level queries (e.g., RPN) and a service to pass non-SPARQL commands.

A plurality of compute nodes 328 can be provided to perform the query operations. In this example, images are received (one image is shown as Image 0 334). The compute nodes can receive, validate and send RPN to all images, and when results are obtained, send those results along with a pointer to an output file. Compute nodes may include a plurality of Operators 336 to perform operations on the images. Operators 336 included in this example are SCAN, JOIN, MERGE, OPTIONAL, UNION, FILTER and BIND, although other operations can be used. These operations can be used to traverse the data in the various database 338 in different ways to fulfill a query. In the example illustrated in FIG. 2, sample query 320 is to identify persons who sell DVDs at shops. The query can be converted (e.g., SPARQL) and submitted to the compute nodes which perform various operations (e.g., operators 336) appropriate for the query to identify people who sell DVDs.

Figure 3:
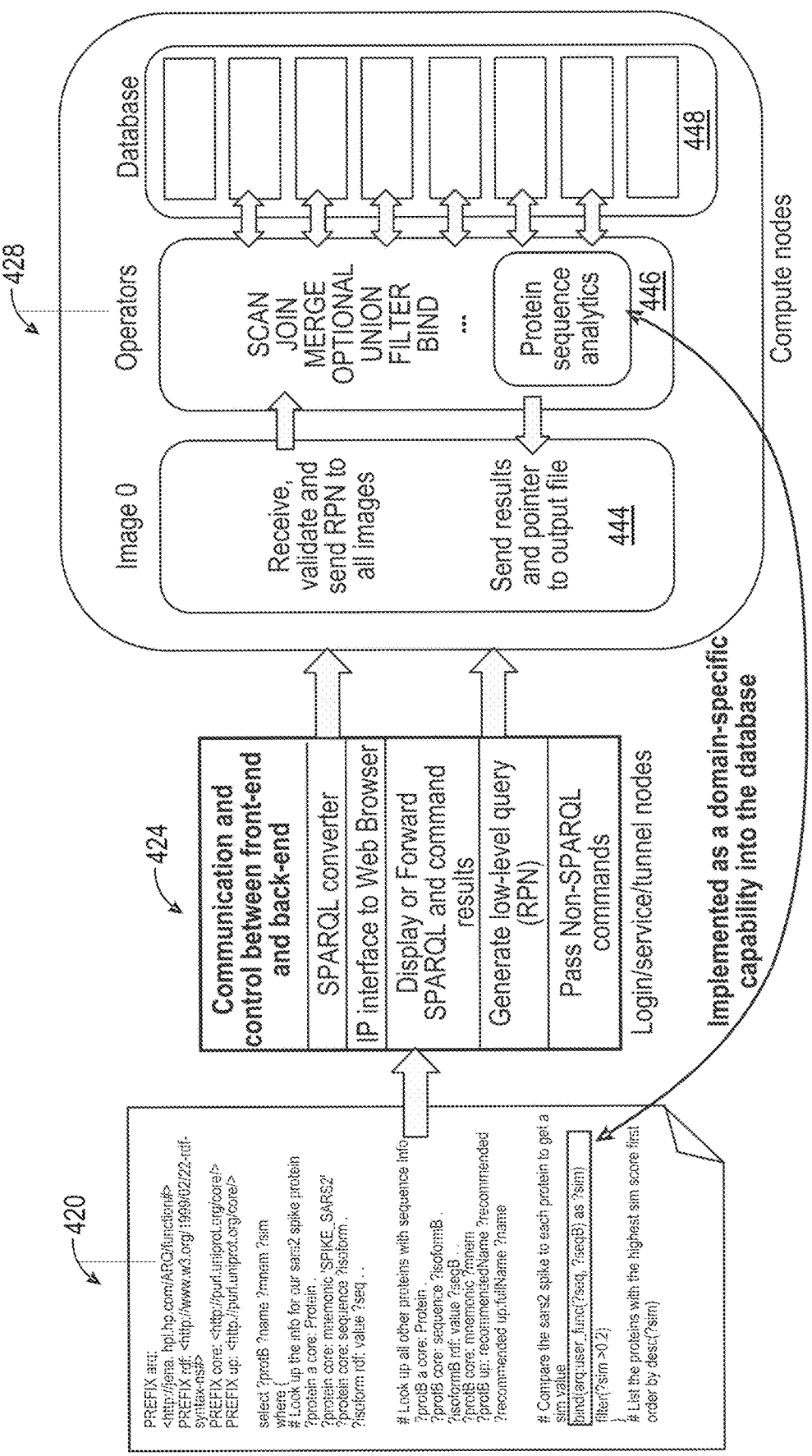
FIG. 3 illustrates an example implementation of a graph engine, such as a CGE, to perform protein sequence analytics in accordance with various embodiments.

In various embodiments, the compute nodes 328 can be improved to perform protein sequence analytics as well. This can be implement as a domain specific capability into the database to provide sequence analytics for various applications including, for example, drug identification and repurpose them. FIG. 3 illustrates an example implementation of a graph engine, such as a CGE, to perform protein sequence analytics in accordance with various embodiments. This example also illustrates a sample query 420 they can be submitted via an interface 424 to compute nodes 428 in the CGE. Like the example of FIG. 3, in this example operators 436 included include SCAN, JOIN, MERGE, OPTIONAL, UNION, FILTER and BIND, among others. However, unlike the example of FIG. 3, in this example operators 436 also include operators to perform protein sequence analytics. In one example, CGE was modified to define an interface for a function that could be used as part of an evaluation expression in operators such as ORDER or FILTER. The function is referred to as a user defined function because the user of CGE can write the function to apply domain specific knowledge to the query results. CGE provides a generic function that users can overwrite with their own function that CGE will load into memory at program startup to use during execution. CGE defines the interface to the function in order to enable passing parameters to the user function and allowing users to return information to CGE for the purpose of evaluating an expression for an operator. The information returned to CGE by the user defined function enables the domain specific function to easily rank or filter results." In various embodiments, the system can be configured such that the user can also be given the ability to add user-defined functions to perform custom searches/queries.

FIG. 4 illustrates an example of a sample query that can be used to perform protein sequence analytics. This can be an example of query 420 introduced above in FIG. 3. As seen in this example, at 442 the example query can include an identification of a protein of the given condition for which a user would like to identify viable therapeutics. In this example, the user identified a SARS2 spike protein, and the query includes a mnemonic, which in this example is 'SPIKE_SARS2'. This portion of the query also identifies the protein sequence for the condition of interest, which in this case is a virus. The core sequence can include all or one or more segments of the protein sequence for the virus.

As also seen in this example, at 454 the query can specify a request to look up all other proteins with the same sequence information. This can include a request to look up the entire sequence or one or more parts of the sequence to see if there are any other proteins with a matching sequence or matching sequence segments. At 455, the query request comparison of the condition of interest (SARS2 Spike) to the other proteins in the database and to provide a similarity score scoring the sequence matches based on their distances. At 457, the query requests that the results be returned and listed with a sort based on similarity scores in descending order.

Figure 5:
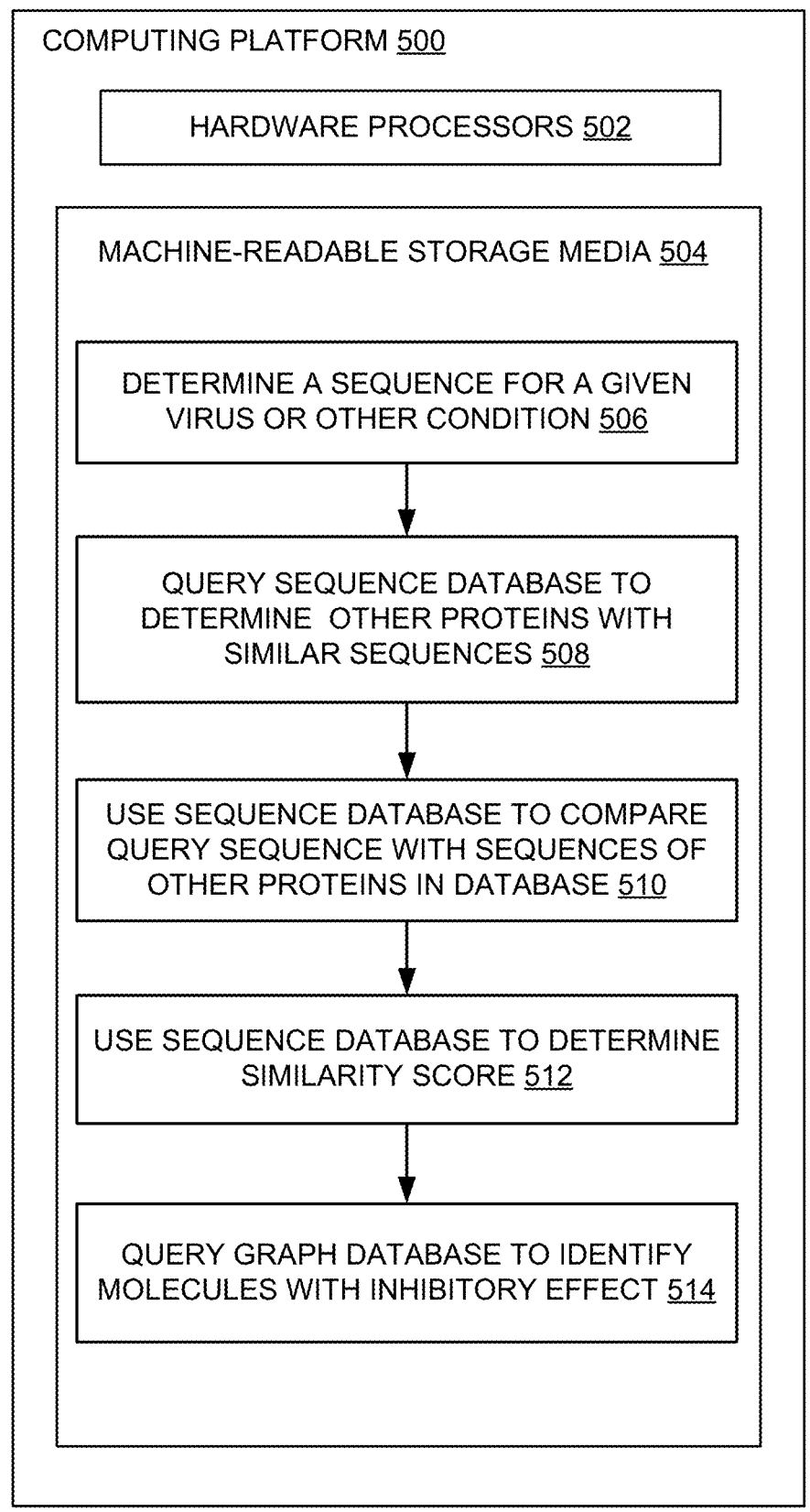
FIG. 5 illustrates an example computing component 500 that may be used to effectuate protein sequence analytics in accordance with various embodiments.

FIG. 5 illustrates an example computing component 500 that may be used to effectuate protein sequence analytics in accordance with one embodiment of the disclosed technology. Computing component 500 may be, for example, a server computer, a controller, or any other similar computing component capable of processing data. In the example implementation of FIG. 5, the computing component 500 includes a hardware processor 502, and machine-readable storage medium 504. Hardware processor 502 may be one or more central processing units (CPUs), semiconductor-based microprocessors, and/or other hardware devices suitable for retrieval and execution of instructions stored in machine-readable storage medium 504. Hardware processor 502 may fetch, decode, and execute instructions, such as instructions 506-514, to control processes or operations for merging local parameters to effectuate protein sequence analytics for rapid-response drug repurposing. As an alternative or in addition to retrieving and executing instructions, hardware processor 502 may include one or more electronic circuits that include electronic components for performing the functionality of one or more instructions, such as a field programmable gate array (FPGA), application specific integrated circuit (ASIC), or other electronic circuits.

A machine-readable storage medium, such as machine-readable storage medium 504, may be any electronic, magnetic, optical, or other physical storage device that contains or stores executable instructions. Thus, machine-readable storage medium 504 may be, for example, Random Access Memory (RAM), non-volatile RAM (NVRAM), an Electrically Erasable Programmable Read-Only Memory (EEPROM), a storage device, an optical disc, and the like. In some embodiments, machine-readable storage medium 504 may be a non-transitory storage medium, where the term "non-transitory" does not encompass transitory propagating signals. As described in detail below, machine-readable storage medium 504 may be encoded with executable instructions, for example, instructions 506-514.

Hardware processor 502 may execute instruction 506 to receive a query including a sequence for a given virus or other condition. For example, a protein or gene sequencing apparatus can be used to determine a sequence for the condition of interest. As described above with respect to the example query in FIG. 4, a query can be built that includes an identification of a protein sequence of the given condition for which a user would like to identify viable therapeutics. The constructed query may also include a mnemonic, and the protein sequence, or segments of the protein sequence, for the condition of interest.

Hardware processor 502 may execute instruction 508 to, in response to the query received, search the sequence database to identify other viruses or proteins with similar sequences to that of the virus (or protein) of interest. As noted above with reference to FIG. 4, the system can search the database to identify matches or similarities to the entire sequence or to one or more identified segments of the sequence. With regard to this operation, hardware processor 502 may execute instruction 510 may compare sequences in the sequence database to the query sequence (the entire sequence or one or more identified segments of the sequence) to determine whether any matches can be identified.

Hardware processor 502 may execute instruction 512 to determine a similarity score based on the comparison. The similarity score can include, for example, a numeric value (e.g., as a number within a defined range or as a percentage, etc.) or other indicator to indicate how similar a given sequence is to the query sequence. For example, if expressed as a percentage, 100% would indicate an exact match. The system may be configured to return results for proteins with similarity scores greater than a given threshold. For example, the system may identify proteins that match with a similarity score of greater than 70% (or some other threshold value). In various embodiments, the threshold level may be set by the query as well.

Hardware processor 502 may execute instruction 514 to query a graph database to identify therapeutics (drugs or molecules) that have an inhibitory effect on the proteins whose sequences have a similarity score greater than the identified threshold. For example, the system may, for each protein having a similarity score greater than the threshold, where the graph database to identify therapeutics that have an effect on those proteins. The system may return the results identifying the therapeutics that have the desired effect and may score the results in accordance with the similarity scores. In other words, therapeutics in the database known to have a desired effect on proteins in the sequence database whose sequence is closest to the sequence of the condition of interest might be deemed to have a higher likelihood of having the desired effect on the condition of interest.

Two core CGE improvements may be included in various embodiments to support drug repurposing: (a) the support for user-defined functions (UDFs) for in-database protein sequence analytics; and (b) the ability to execute such domain-specific UDFs in parallel for speedup and scale-out using the SPARQL front-end user interface described above.

The syntax for user-defined functions in CGE may follow Apache Jena guidelines, for example, because CGE leverages Jena's SPARQL query parser interface. The SPARQL interface allows custom functions inside query ex-pressions to enable domain specific operations on data as part of a query. This is a feature that allows users to define, express and execute domain-specific mathematical operations to evaluate and rank query results that are not supported in SPARQL. Such graph operations can be implemented as custom functions that are defined by URI in expressions. This capability may be configured to allow users to define their own function. Calls to these user-defined functions may take the form:

```
prefix arq: <http://jena.hpl.hp.com/ARQ/function#>
...
arq:sqrt (5)
...
```

Two custom user defined functions (UDF) for drug repurposing, a new URI, arq:user_func, may be included in CGE to invoke a callout to a UDF that exists separately from CGE. A simple C interface may be defined for a function named cge_user_eval that CGE can execute as part of an expression. The cge_user_eval function takes four arguments that provide the total number of arguments, a list of the arguments, the return value and the return type. This may allow users to pass data from CGE to the UDF, evaluate the arguments, and return a primitive value (e.g., boolean, integer or double) that can be used to evaluate the SPARQL expression.

Because CGE executes in a massively parallel manner, with potentially tens of thousands of images running concurrently, any UDF invoked as part of a query may also be executed in parallel on the query solution set. The parallel execution of the UDF may enable it to scale to datasets that may otherwise be too large by dividing the data across the parallel images. A UDF can also be applied to the entire solution set in an embarrassingly parallel manner. Further, the parallel execution via UDFs may enable distributed execution of computationally intensive algorithms by breaking down complex processing tasks into images that will have a considerably smaller input set to process.

Embodiments may include enhancements to CGE focused on improving the performance of database operations such as FILTER or GROUP. These operations may enable users to compare terms that are found as part of a query match to apply some order or ranking. The raw strings for these terms may be stored in the CGE dictionary, which may be implemented as a distributed hash table that spreads the strings across all processes. This distribution of the terms results in significant work pulling terms local to a process when they are needed as part of an operation, such as FILTER or GROUP.

To improve the overall performance and scalability of these operations, the strings used by images may be fetched as large blocks in a coordinated manner. Each image may go through the results and create a list of strings it requires from each other image. All images may then fetch the required strings from each other as a single block, rather than issue a remote fetch of each string individually. This increases the size of each message but significantly reduces the total number of messages required. This communication pattern matches what is done in CGE for the core graph operations, such as JOIN and MERGE, and has been shown in previous studies to significantly improve performance by reducing the number of outstanding messages at a time [8]. This CGE improvement is critical for parallel pairwise comparisons of a query protein sequence with millions of open-science sequences and rank-ordering the result set.

Embodiments integrate a life sciences knowledge graph using biomedical or other life sciences data resources. For example, implementations may use a set of available biomedical data resources normally used in life sciences and systems biology research for the knowledge graph. A typical workflow for researchers is to perform searches in one of the databases, then construct queries for another database, and iterate. The effort of manually mapping between the ontologies of various data sources and piecing together results from multiple query end points (or using yet another database to perform this translation), is a cumbersome process. In various embodiments, the scalability of CGE enables all of the relevant databases to be loaded in one environment, enabling seamless cross-database queries. Federated queries may also be used to query across multiple databases in various embodiments, however, this approach may not be well suited to complex queries due to challenges such as network access from firewalled systems, query rate limits or simply performance problems of complex federated queries. The scalable load time of CGE also enables frequent reloads of the data set, including integration of in-house data on top of a background of the public databases during the workflow. Further, the performance and scalability of CGE for the database build process enables updated data to be quickly pulled in and the database fully rebuilt in less than an hour.

The integrated Life Sciences knowledge graph assembled to study potential drug repurposing candidates for COVID-19 was generated from a collection of publicly available databases. Descriptions of the larger databases in the collection, and those explicitly mentioned in this document, are now described.

Uniprot: The UniProt database is a collection of functional information on proteins, and includes annotations, interrelationships, and in some cases, the amino acid sequences of the proteins themselves. Proteins are the building blocks used for studying drug protein structure and interactions. The interactions between proteins are complex and widely linked, so a graph representation is particularly useful. Uniprot concentrates on Human proteins, though other widely studied organisms are also well represented.

The UniProt Consortium is a collaboration between the European Bioinformatics Institute (EBI), the Swiss Institute of Bioinformatics (SIB) and the Protein Information Resource (PIR). It has been a pioneer in Semantic Web technology, and Uniprot has been distributed in RDF format since 2008. Uniprot is continually growing as more scientific data is added. New Uniprot releases are distributed every four weeks.

For this study, the majority of the Uniprot RDF data is from the Mar. 19, 2020 release. There is a new UniProt portal for providing the latest information for COVID-19 coronavirus protein entries and receptors which is updated independently of the general UniProt release cycle. For the COVID-19 study this allowed us to more quickly pull in updated COVID data. The COVID-19 Uniprot data for the knowledge graph was updated May 22, 2020. The Uniprot database contains approximately 87.6 Billion triples. In the form of an N-Triples (.nt) file on disk it is roughly 12.7 Terabytes. To simplify querying across multiple databases, we merged all named graphs into a single default graph.

PubChem: PubChem is an open chemistry database maintained by the National Institutes of Health (NIH). The PubChemRDF project provides RDF formatted information for the PubChem Compound, Substance, and Bioassay databases. The knowledge graph for this study used the V1.6.3 beta version of PubChemRDF download from ftp://ftp.ncbi.nlm.nih.gov/pubchem/RDF on Mar. 30, 2020. The PubChemRDF database contains approximately 80 Billion RDF triples. In the form of N-triples this amounts to about 13 Terabytes on disk.

ChEMBL: ChEMBL is a manually curated database of bioactive molecules with drug-like properties. It brings together chemical, bioactivity and genomic data to aid the translation of genomic information into effective new drugs. The data is updated regularly, with releases approximately every 3-4 months. ChEMBL-RDF Release 27.0 (May 18, 2020) was integrated into the knowledge graph for this study. The ChEMBL database contains approximately 539M triples. In the form of N-triples this amounts to about 81 Gigabytes on disk.

Bio2RDF datasets: Bio2RDF is an open-source project that uses Semantic Web technologies to pull together a diverse set of datasets from multiple data providers. In addition to providing an online Virtuoso-based SPARQL endpoint for querying across the collection of heterogeneous datasets, Bio2RDF also provides a portal to download the converted RDF data files for datasets included in the Bio2RDF database. The Bio2RDF datasets included in the knowledge graph were downloaded from.

The full Bio2RDF collection consists of approximately 11 Billion triples across 35 datasets and includes the DrugBank, PubMed, and MESH datasets.

OrthoDB: OrthoDB (https://www.orthodb.org) provides evolutionary and functional annotations of orthologs, i.e. genes inherited by extant species from their last common ancestor. Since orthologs are the most likely candidates to retain functions of their ancestor gene, OrthoDB is aimed at narrowing down hypotheses about gene functions and enabling comparative evolutionary studies.

The OrthoDB database contains approximately 2.2 Billion RDF triples describing evolutionary and functional properties of 40 Million genes from 15 thousand organisms. In the form of N-triples this amounts to about 275 Gigabytes on disk.

TABLE I

KNOWLEDGE GRAPH DATASET CHARACTERISTICS.
RAW SIZES BEFORE DUPLICATE REMOVAL.

| Dataset | Size (on disk) | Size (triples) | source |
|---|---|---|---|
| UniProt (March 2020) | 12.7 TeraBytes | 87.6 Billion | [7] |
| PubChemRDF (v1.6.3 beta) | 13.0 TeraBytes | 80.0 Billion | [12] |
| ChEMBL-RDF (27.0) | 81 GigaBytes | 539 Million | [13] |
| Bio2RDF (Release 4) | 2.4 TeraBytes | 11.5 Billion | [14] |
| OrthoDB (v10) | 275 GigaBytes | 2.2 Billion | [17] |
| Biomodels (r31) | 5.2 GigaBytes | 28 Million | [20] |
| Biosamples (v20191125) | 112.8 GigaBytes | 1.1 Billion | [21] |
| OLS (March 2018) | 10.2 GigaBytes | 78.8 Million | [22] |
| Reactome (r71) | 3.2 GigaBytes | 19 Million | [23] |

BioModels: The BioModels database is a repository of mathematical models representing biological systems. It currently hosts a range of models describing processes like signaling, protein-drug interaction interactions, metabolic pathways, epidemic models and many more. The models that BioModels hosts are usually described in peer-reviewed scientific literature and in some cases, they are generated automatically from pathway resources (Path2Models). These models are manually curated and semantically enriched with cross-references to external data resources (such as publications, databases of compounds and pathways, ontologies, etc.)

Embodiments provide the capability of CGE to support UDFs, may be implemented such that queries may be written that combine information from the knowledge graph and apply domain specific UDFs to the data in order to better refine results. For drug repurposing, embodiments may implement a UDF that performs protein sequence similarity to infer connections between proteins. This may be configured to enable connections to be inferred between proteins that little may be known about, such as COVID-19, and proteins that are well documented in open datasets such as Uniprot and ChEMBL.

Embodiments may utilize the Smith-Waterman (SW) protein similarity algorithm for aligning pairs of sequences and computing similarity scores for the alignment. For two sequences of length m and n, the SW algorithm returns the optimal local alignment and similarity score with a computational time complexity of $O(mn)$. The local alignment is useful for providing alignments describing the most similar regions within sequences, rather than end-to-end alignments of sequences returned by global alignments. Since SW returns an optimal local alignment it is an essential component of many aligners. However, the computational complexity limits the extent the algorithm is utilized for comparing large sequence sets.

The SW algorithm may be desirable in various embodiments because of the preference to score similarity using optimal local alignment and the availability of a highly optimized open source implementation as a standalone C/C++ library that could be loaded by CGE [25]. Given the highly parallel implementation of CGE, a user can query the knowledge graph and perform millions of protein similarity computations in a matter of seconds, enabling the solutions to easily be filtered and ranked by similarity score.

To normalize the scores, each sequence may be compared to itself. The product of the square root of those scores is used as the denominator as outlined in listing 1.

Listing 1. Normalization method of Smith-Waterman scores

```
int64_t score = prot_cmp( ref , read );
int64_t max_ref_score = prot_cmp( ref , ref );
int64_t max_read_score = prot_cmp( read , read );
double norm_score = score /
    ( sqrt ( max_ref_score ) * sqrt ( max_read_score ) )
```

Embodiments of the systems and methods described herein may allow researchers to understand how similar or different the novel coronavirus is to other known viruses. If parts of the protein sequence that make up the novel virus have sequence and functional overlaps with other known viruses, the information in the integrated knowledge graph helps us extrapolate the search to identify potential drug candidates that are known to inhibit disease-causing activity on the known viruses. Simple example queries that implement the similarity-based extrapolation in the following paragraphs are now provided.

COVID-19 Similarity: The COVID-19 protein sequence is made up of several non-structural proteins, envelope proteins, Spike protein, etc. To hypothesize potential drugs that bind or interact with the different parts of the COVID-19 viral protein, embodiments may first identify open-science proteins that have similar structure to the novel COVID-19 mutation. The query in listing 2 is an example to find proteins most similar to the COVID-19 Spike protein sequence.

Listing 2. SPARQL query to rank similar proteins to reference protein

```
select ?protB ?name ?mnem ?sciName ?sim
where {
    # Look up the info for our protein of interest
    ?protein a core : Protein ;
        core : mnemonic 'SPIKE_SARS2' ;
        core : sequence ?isoform .
    ?isoform rdf : value ?seq .
    # Look up all other proteins with sequence info
    ?protB a core : Protein :
        core : sequence ?isoformB ;
        core : mnemonic ?mnem :
        up : recommendedName ?recommended .
    ?isoformB rdf : value ?seqB .
    ?recommended up : fullName ?name .
    # Optionally . look for the scientific name of the organism. This
    # may not exist if the protein data is too new , such as for covid -19.
    so
    # make it optional so we still get the match .
    optional {
        ?protB up: organism ?taxon .
        ?taxon core : scientificName ?sciName .
    }
    # Compare the protein of interest to each protein to gel a sim value
    bind( arq : user_func(?seq , ?seqB ) as ?sim )
    filter(?sim >= 0 . 1 )
}
# List the proteins with the highest sim score first
order by desc(?sim )
```

The example similarity query in listing 2 first looks up the protein sequence for SPIKE_SARS2 using the Uniprot mnemonic. Next, the sequences for all proteins that have sequences and names are retrieved. Finally, each of these sequences is compared to the sequence for the SPIKE_SARS2 and the similarity score is saved in the variable sim. The bind clause saves all of the sim values in a temporary table so that they can be used for other operations and returned to the user. In this query, any result with a similarity score less than 0.1 is removed and the results are returned in descending order by the similarity score.

The protein returned with the highest similarity score was A0A2D1PX97, which is "Bat SARS-like coronavirus", with a similarity score of 0.817. Several of the top results are bat coronaviruses or coronaviruses in other species, as shown in the top 10 results listed in table II. The similarity scores quickly drop from 0.79 to 0.37, which is the point where Middle East Respiratory Syndrome (MERS) first appears in the results with a similarity score of 0.368 for protein A0A2I6PIX8, which is "Middle East respiratory syndrome-related coronavirus". Following several proteins for MERS are a number of coronaviruses in other species, including bovine, human, rabbit and murine, and several non-coronavirus proteins begin appearing such as A0A1B2RX89 for "Infectious bronchitis virus" with a similarity score of 0.322. These scores match up well with research that has suggested that COVID-19 likely originated from bats and has a close similarity to MERS [27].

TABLE II

TOP 10 PROTEIN SEQUENCES MOST SIMILAR TO COVID-19 SPIKE

| Protein | Scientific Name | Score |
|---|---|---|
| A0A2D1PX97 | "Bat SARS-like coronavirus" | 0.817 |
| A0A0U21WM2 | "SARS-like coronavirus WIV16" | 0.817 |
| A0A2D1PXA9 | "Bat SARS-like coranavirus" | 0.816 |
| U5WLK5 | "Bat SARS-like coronavirus RxSHC014" | 0.814 |
| A0A2D1PX29 | "Bat SARS-like coronavirus" | 0.814 |
| U5WHZ7 | "Bat SARS-like coronavirus Rs3367" | 0.813 |

TABLE II-continued

TOP 10 PROTEIN SEQUENCES MOST SIMILAR TO COVID-19 SPIKE

| Protein | Scientific Name | Score |
|---|---|---|
| U5W105 | "Bat SARS-like coronavirus WIV1" | 0.813 |
| A0A2D1PXC0 | "Bat SARS-like coronavirus" | 0.813 |
| A0A2D1PXD5 | "Bat SARS-like coronavirus" | 0.812 |
| A0A4Y6G147 | "Coronavirus BtRs-BetaCoV/YN2018B" | 0.812 |

COVID-19 Drug Repurposing: after the similarity analysis results are obtained, embodiments may be implemented to leverage the knowledge graph to find potential drugs that could be repurposed for COVID-19 based upon the similarity score rankings. To do this a SPARQL query is used that is configured to work in reverse-rather than looking for all known targets of a given compound the query starts with an unknown protein and searches for potential compounds that could target it. In this case the example focuses on compounds that would have an inhibitory action on the proteins. The example query in listing 3 may be used to do this search.

Listing 3. SPARQL query to find potential drugs that could be repurposed

```
select distinct ?protB ?sciName ?label ?sim
    where {
    {
        # Look up activities with an inhibitory effect that have small
        # molecules and have gone through a certain development phase
        select ?activity ?assay ?label
            where {
            { ?activity cco : type ' Inhibition ' } union { ?activity cco :
            type
            ' IC50 ' }
            ? activity a cco : Activity :
                cco : hasMolecule ?molecule ;
                cco : hasAssay ?assay .
            ?molecule rdf : type cco : SmallMolecule ;
                cco : highestDevelopmentPhase ?phase :
                skos : prefLabel ?label .
            filter (?phase >= 3 )
        }
    }
    # Look up proteins that have a sequence , compare to our sars2
    # protein . and select only the top X proteins based similarity
    {
        select distinct ?protB ?sim
            where {
            # Look up the sequence for the sars2 spike protein
            ?protein a core : Protein ;
                core : mnemonic 'SPIKE_SARS2 ' :
                core : sequence ?isoform .
            ?isoform rdf : value ?seq .
            # Look up activities that target proteins. We do this here to
            # make sure we only select proteins that are known targets
            ?targetcmpt cco : targetCmptXref ?protB .
            ?target cco : hasTargetComponent ?targetcmpt .
            ?assay cco : hasTarget ?target .
            # Look up known proteins and get sequence values
            ?protB a core : Protein ;
                core : sequence ?isoformB .
            ?isoformB rdf : value ?seqB .
            bind ( arq : user_func( ?seq , ?seqB ) as ?sim )
        }
        order by desc ( ? sim )
        limit 150
    }
    # Look up our compounds that target our proteins of interest , if any
    # do. This is a repeat from the inner-protein query because we do
    # not want the inner query to generate combinations for
    # proteins/compounds when finding the most similar proteins.
    # Redoing the joins here is quick.
    ?targetempt cco : targetCmptXref ?protB .
    ?target cco : hasTargetComponent ?targetempt .
    ?assay cco : hasTarget ?target .
    # Optionally . look for the scientific name of the organism .
```

Listing 3. SPARQL query to find potential drugs that could be repurposed

```
    optional {
       ?protB up : organism ?taxon .
       ?taxon core : scientificName ?sciName .
    }
}
order by desc(?sim )
```

There are three main components to this example query. First, the top inner-query searches ChEMBL for information about compounds that have an inhibitory activity that have been through a certain development phase. Because the intent is to repurpose existing drugs, the compounds may be limited to only those that are in phase 3 development or higher for clinical trials. In the second inner query, all proteins that are known targets of a given compound are compared to the COVID-19 Spike protein. The results are put into descending order by the similarity to the SPIKE_SARS2 protein and only the proteins for the top 150 isoforms are returned. There are often multiple sequences for a given protein and in this case, the top 150 isoforms are associated with approximately the top 50 most similar proteins. The final part of the query again matches the selected proteins to the compounds that target them as well as the activity information from the first inner query. The final results are returned in descending order by the similarity score to highlight compounds that could potentially be repurposed based on similarity to the COVID-19 spike.

The reverse query returns compounds targeting proteins with similarity scores ranging from 0.2 down to 0.183. Several of these compounds are for drugs that have already been put into clinical trials because of their potential to be repurposed against COVID-19 [29]. Some of the top scoring protein sequences against the COVID-19 spike found by the reverse query that are also in clinical trials are shown in table III.

TABLE III

EXAMPLE DRUGS CURRENTLY IN CLINICAL TRIALS FOR COVID-19 THAT APPEAR IN REVERSE QUERY RESULTS

| Protein | Compound Name | Score |
| --- | --- | --- |
| P52333 | BARICITINIB | 0.194 |
| P17948 | RIBAVIRIN | 0.189 |
| P17948 | RITONAVIR | 0.189 |
| P17948 | DEXAMETHASONE | 0.189 |
| P17948 | AZITHROMYCIN | 0.189 |
| P08183 | LOPINAVIR | 0.187 |

One method we have used to validate the results returned by the reverse query is to compare the overlap between the compounds returned with those currently in clinical trials for COVID-19. Based on the drugs currently part of clinical trials in early June, we created a list of 196 unique drugs to compare our results against. For the above query considering the top 150 isoform sequences most similar to the SPIKE_SARS2 protein, the results returned by the knowledge graph include 91 of the 196 compounds (46%). The significant overlap between compounds found by the reverse query with the clinical trials list also helps define the range of scores that could be considered interesting. Since the proteins found by the reverse query all have similarity scores between 0.183 and 0.20, it seems reasonable that compounds targeting other proteins with scores in the same range could have a beneficial impact against COVID-19 as well.

A New Hypothesis-Tetanus: One potentially interesting result returned by the reverse query using the SPIKE_SARS2 is tetanus toxin, which has the Uniprot identifier P04958 and mnemonic TETX_CLOTE. The reverse query against the spike returns TETX_CLOTE as the highest match with a similarity score of 0.20. Given the large rate of asymptomatic positive COVID-19 cases, which the Centers for Disease Control and Prevention (CDC) currently estimates to be 40% [30], the TETX_CLOTE result caused one unexpected, but interesting hypothesis—that the tetanus vaccine could be contributing to the asymptomatic rate by enabling the immune system to generate a reasonable response to the virus and reduce the severity of symptoms. According to the CDC, in 2017 approximately 63.4% of adults 19 and older in the US had received some form of the tetanus vaccine within the last 10 years as recommended, with a notable decline in individuals greater than 65 years old. While tetanus is caused by a bacteria and COVID-19 is a virus, there are multiple examples of heterologous immunity between bacteria and viruses. This heterologous immunity has at least initially been attributed to amino acid sequence similarities of T and B cell epitopes for antigens of different pathogens.

Database Performance

To facilitate COVID-19 research, the Life Science knowledge graph was hosted on a small number of the larger Cray XC-40 development systems. These systems primarily contained a mix of Intel Broadwell, Skylake and Cascade Lake processors. The files containing the N-Triples used to build the database as well as the built database are stored on the attached Lustre filesystem and striped to match the available number of object server targets (OSTs) in the file system.

The performance results in this section were run on an internal 370 node XC-40 development system (336 compute nodes, 34 service nodes) with a mix of dual-socket 48-core Skylake nodes, and 48-core and 56-core Skylake nodes, ranging in frequency from 2.1-2.4 GHz. The majority of these nodes have 192 GB DDR-2666 memory but 63 of the Cascade Lake nodes have the larger 384 GB DDR4-2933 memory. The attached Lustre file system is a Sonexion CS-L300N system with 8 OSTs providing 655 TB of storage. Database build and load times are dominated by I/O performance to/from the Lustre filesystem so I/O system performance is an important consideration. Query execution time reported is the strict query time and does not include the time required for writing the results to the Lustre file system which is common practice.

Database Build: As previously mentioned in the CGE background section, the first step done by CGE is to build a database from a set of input N-Triple/N-Quad files to produce the compiled database in the representation used by the query engine. The raw N-Triples input files used for the life sciences database are 28.29 TB on Lustre. The build process is handled by the dictionary component of CGE and consists of several steps, which are outlined in Table V along with the times (in seconds) for each step.

TABLE V

TIMES OF BUILD STEPS FOR LIFE SCIENCES DATABASE

| Build Step | 128 nodes × 16 images per node Times (seconds) | 256 nodes × 16 images per node Times (seconds) |
|---|---|---|
| Read | 1937.04 | 1613.16 |
| Ingest | 385.10 | 180.61 |
| Sync | 51.88 | 27.34 |
| Update | 380.87 | 154.35 |
| Total Build | 2157.89 | 1975.46 |
| Checkpoint | 422.09 | 375.35 |

As the numbers show, the build time for the database is dominated by the time to read the raw N-Triples files from Lustre, which is expected. The times for the remaining build steps (i.e., Ingest, Sync and Update) scale well from 128 (2048 images) to 256 nodes (4096 images). A checkpoint of the built database is written to Lustre so subsequent restarts of CGE with the same database can load the compiled database rather than having to ingest the raw N-Triples again. The built database is only ~5.4 TB on disk, versus the ~28.29 TB of raw N-Triples, and CGE can be restarted with the built database in approximately 568 seconds on 256 nodes with 16 images per node.

Spike Similarity Query: The first query used to test the performance of CGE with the life sciences knowledge graph was the similarity query from listing 2. This query searches the known proteins from Uniprot that met certain conditions, such as having a sequence value and a recommended name, and compares them to the sequence value for the SPIKE_SARS2. The similarity query finds 49,299,877 protein sequences to compare against the SPIKE_SARS2 sequence. Table VI shows the times for computing the SW calculations for the 49.3 million protein sequences as well as the total query time when executing on 128 and 256 nodes using either 16 or 32 images per node.

Looking at the times for the SW calculations we observe that the time to compute similarity scales well by both image count (i.e., cores) as well as node count. This is attributed to the fact that calculation is independent of the others so all images can compute the calculations for a subset of the protein sequences in parallel. The scaling also highlights the advantage of utilizing the SW calculation within the massively parallel context of CGE. If a knowledge graph executing on a single process performed the same SW calculations it would take ~21,709 seconds (i.e., 10.6×2048), essentially making the query impossible in a serial context. The strict query times do show reasonable scaling from 128 to 256 nodes, at least at 16 images per node, but the scaling of the query is limited by performance limitations of the GROUP operator. Since the similarity scores are rounded to three decimal places there are a large number of repeat values, which need to be removed when storing the values as new variables within CGE (i.e., ? sin query variable). Due to how CGE distributes these new variables across images the large number of repeats can result in several images waiting for a small number of images to finish processing the values they will store. Further, the query scaling is also related to the recent performance improvement made to enable operations such as GROUP and FILTER to fetch the required strings as blocks, rather than individually. The protein sequences can be quite long, ranging from hundreds to several thousand amino acids, so the fetching of these long strings as blocks from remote processes is crucial to prevent communication overhead from dominating the query performance.

Spike Reverse Query: The next query used to test the performance of CGE on the life sciences knowledge graph was the reverse query from list 3. This query starts at the protein sequence for SPIKE_SARS2 and searches for similar proteins that are targets of acceptable compounds that have the desired affect (i.e., inhibitory). The reverse query is considerably more complex than the similarity query because of the number of joins that must be done on the large intermediate results to find only the proteins or compounds that are desired. While the complex joins impacts the overall query time, the extra conditions imposed by the joins significantly reduces the number of protein sequences that must be compared. CGE has been optimized to filter out solutions early in the query during the scan and join phases by reusing information from previous portions of the query. This optimization may be used to reduce the size of the intermediate results that must be joined, which is useful for not only performance but also memory requirements for queries as complex as the reverse query. For the case of the SPIKE_SARS2 reverse query, the number of proteins compared is only 1,165,914, which is much smaller than the 49.3 million proteins compared in the similarity query.

As the numbers show in Table VII, the SW times are a very small portion of the query time due to the abilities of CGE to leverage information within the knowledge graph to significantly reduce the number of proteins considered. The strict query time for the reverse query is more than double the time for the similarity query, which is expected because of the larger number of complex joins in the reverse query. The majority of the strict query time is dominated by the join. For example, on 256 nodes with 16 images per node the strict query time is 49.0 seconds and 34.52 seconds of that is spent doing the joins. Even with the complex joins, the performance from 128 to 256 nodes scales reasonably well when using 16 images per node (1.82× speedup), but while the query is faster with 32 images per node the scaling is not as efficient. The limited scaling with more cores per node is related to memory access bottlenecks caused by images accessing memory on the same node but on a different socket.

Because there are no other known large semantic graph engines capable of loading a real world life science dataset of this magnitude the performance of CGE cannot be easily compared with other database engines. However, previous benchmarks have clearly demonstrated with the standard LUBM trillion triples dataset that CGE is at least an order of magnitude faster than any competitor, especially when performing complex queries [8]. For the case of LUBM the typical benchmark query is number 9, which does multiple complex joins to search the dataset for a certain triangular relationship amongst entities [9].

TABLE VI

SCALING RESULTS FOR SPIKE SIMILARITY QUERY

| Nodes | Images/ Node | Total Images (Threads) | Time for Protein Similarity calculation (seconds) | Strict Query Time (seconds) |
|---|---|---|---|---|
| 128 | 16 | 2048 | 10.6 | 27.0 |
|  | 32 | 4096 | 5.6 | 21.6 |
| 256 | 16 | 4096 | 5.2 | 18.2 |
|  | 32 | 8192 | 2.7 | 17.6 |

TABLE VII

SCALING RESULTS FOR REVERSE QUERY

| Nodes | Images/Node | Total Images (Threads) | Time for Protein Similarity calculation (seconds) | Strict Query Time (seconds) |
|---|---|---|---|---|
| 128 | 16 | 2048 | 0.58 | 89.4 |
|  | 32 | 4096 | 0.33 | 60.0 |
| 256 | 16 | 4096 | 0.21 | 49.0 |
|  | 32 | 8192 | 0.08 | 37.3 |

Scalability Advantages: The performance and scalability of CGE has been demonstrated in previous studies [8], [10] as well as in the results discussed above. This performance at scale is critical when trying to search such large datasets interactively. While smaller graph engines could be leveraged to analyze the same data, the time required to perform even simple queries would almost certainly be too high to make the system useful. The ability of CGE to scale to hundreds of nodes and tens of thousands of images enables very large datasets to be ingested quickly and searched in seconds, even when performing the most complex queries across the graph. This scalability is also very advantageous for UDFs because it enables domain specific functions, some of which may be computationally complex, to easily be applied for improved refinement of the query results. These unmatched capabilities of CGE [8] give researchers the ability to search very large, real world datasets in order to find compounds that could be effectively repurposed in real time.

Insights on the Drug Repurposing Problem

While this study focused primarily on the application of the knowledge graph and SW sequence comparison to COVID-19, the changes and queries could be applied to any number of diseases of interest. For example, if the SPIKE_SARS2 mnemonic from the similarity query in listing 2 were changed to USTGX1_COWPX, which is a Uniprot mnemonic for cowpox virus, the similarity query could be used to find the proteins most similar to the given cowpox. In this case, running that similarity query returns multiple cowpox viruses as the top three results, followed by a taterapox and then three camelpox viruses. More interesting results start showing up at number seven on the similarity list, which is Uniprot mnemonic V5QZD2_9POXV for the protein V5QZD2 for "Vaccinia virus WAU86/88-1", with a similarity score of 0.892. Vaccinia virus has been used more for human immunizations than any other vaccine due to its similarity to variola virus, which is the causative agent of smallpox.

The reverse query could also be used for other diseases to search for potential drugs that could be repurposed. For example, replacing the SPIKE_SARS2 mnemonic with the Uniprot mnemonic KITH_HHV11, which is for "Human herpesvirus 1" (HHV1), returns Brivudine as the top compound for inhibiting protein P06479 with a similarity score of 0.984. Brivudine is known to have a strong antiviral activity against varicella-zoster virus and herpes simplex virus type 1 [44]. The top 10 query results are all in fact for various HHV1 proteins with compounds such as Penciclovir and Acyclovir, which are known antivirals that target herpes simplex virus type 1 [44], [45].

These results clearly demonstrate the ability of CGE to enable the knowledge graph with the SW sequence similarity UDF to quickly and effectively find potential drugs that could be repurposed to target a different disease. These abilities of CGE can allow researchers to interactively search for potential candidates and apply subject matter expertise to further refine the query results to possibly increase the effectiveness of re-targeted drugs.

The examples described herein demonstrate how CGE, a massively parallel semantic graph engine, and other similar engines, can easily ingest and search a graph database of this scale and enable researchers to perform complex queries across the datasets in seconds. Further, the performance of CGE gives researchers the ability to interactively query the given database of 155 billion triples to search for potentially hidden connections between nodes of the graph that would otherwise be impossible to find.

This paper also discussed recent changes made to CGE to enable user defined functions that allow users to apply domain specific expertise to operations such as FILTER, GROUP and ORDER. Our work focused on leveraging an open source implementation of the Smith-Waterman sequence similarity algorithm as a UDF within a query to apply ranking to proteins targeted by a known compound based on the similarity to a given reference sequence. Using the SPIKE_SARS2 protein as a reference we showed how a query could be written that enabled CGE to find potential drugs that could be repurposed for COVID-19 in a matter of seconds. Additionally, we demonstrated that these abilities of CGE are not specific to COVID-19 and could easily be used to find potential drugs to repurpose for other known or new diseases of interest.

Using our two main queries of interest we demonstrated the strong scaling of the Smith-Waterman function within a query and showed good overall scaling for the queries themselves. The scaling tests showed some future areas to focus on for improving scaling. First, the GROUP operator has performance bottlenecks caused by too many duplicates being generated and the queries did not scale as well as desired with increased core counts. However, even with these limitations we were able to show good scaling for the complex queries, further demonstrating the unique capabilities of CGE.

Finally, we have shown that the unique capabilities of CGE, including massive parallelism, complex query performance and the scale of data that can ingested, combined with a protein sequence similarity can enable researchers to quickly and effectively repurpose existing drugs to target new diseases.

Figure 6:
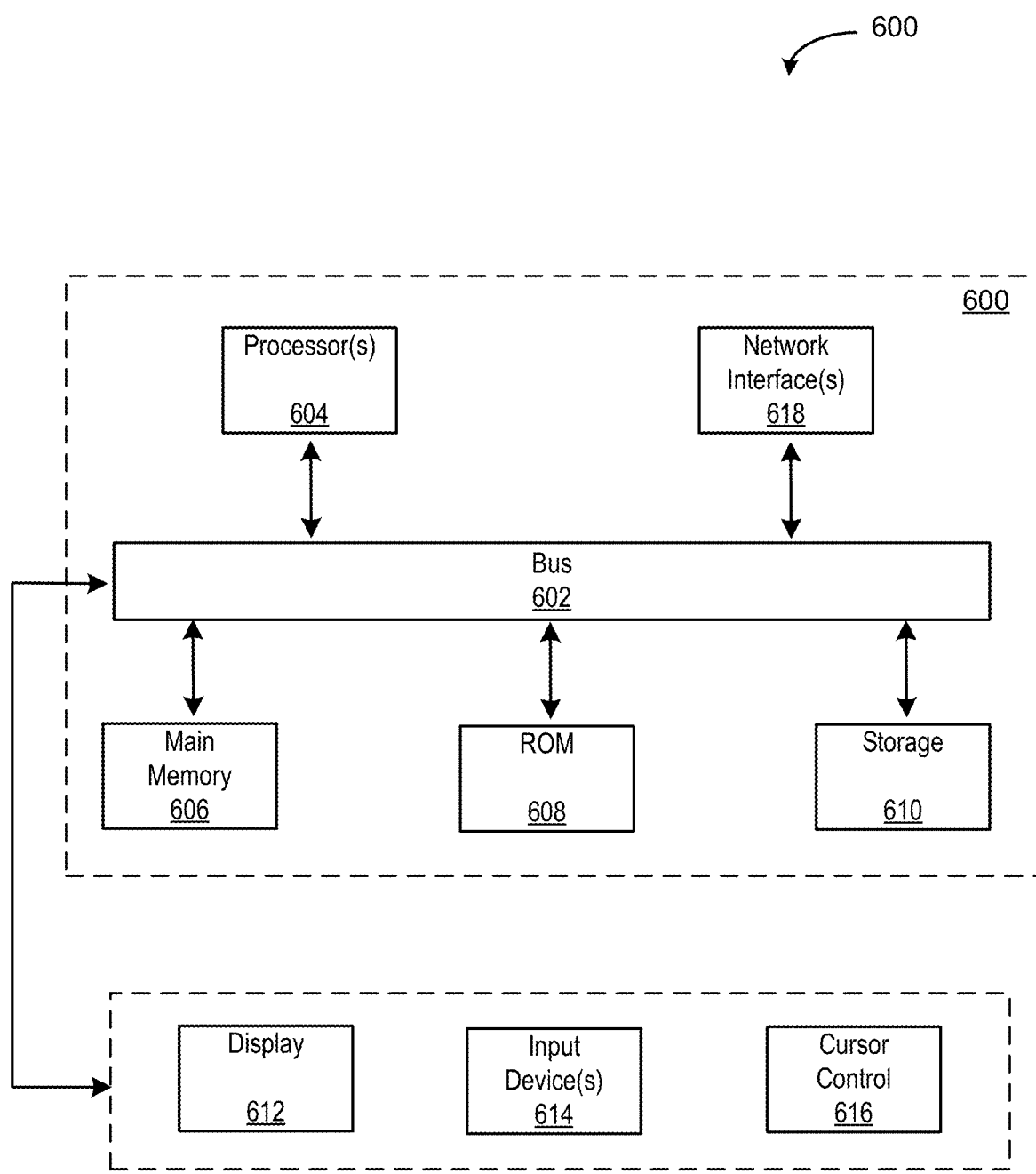
FIG. 6 is an example computing component that may be used to implement various features of embodiments described in the present disclosure.

FIG. 6 depicts a block diagram of an example computer system 600 in which various of the embodiments described herein may be implemented. The computer system 600 includes a bus 602 or other communication mechanism for communicating information, one or more hardware processors 604 coupled with bus 602 for processing information. Hardware processor(s) 604 may be, for example, one or more general purpose microprocessors.

The computer system 600 also includes a main memory 606, such as a random access memory (RAM), cache and/or other dynamic storage devices, coupled to bus 602 for storing information and instructions to be executed by processor 604. Main memory 606 also may be used for storing temporary variables or other intermediate information during execution of instructions to be executed by processor 604. Such instructions, when stored in storage media accessible to processor 604, render computer system 600 into a special-purpose machine that is customized to perform the operations specified in the instructions.

The computer system 600 further includes a read only memory (ROM) 608 or other static storage device coupled to bus 602 for storing static information and instructions for processor 604. A storage device 610, such as a magnetic disk, optical disk, or USB thumb drive (Flash drive), etc., is provided and coupled to bus 602 for storing information and instructions.

The computer system 600 may be coupled via bus 602 to a display 612, such as a liquid crystal display (LCD) (or touch screen), for displaying information to a computer user. An input device 614, including alphanumeric and other keys, is coupled to bus 602 for communicating information and command selections to processor 604. Another type of user input device is cursor control 616, such as a mouse, a trackball, or cursor direction keys for communicating direction information and command selections to processor 604 and for controlling cursor movement on display 612. In some embodiments, the same direction information and command selections as cursor control may be implemented via receiving touches on a touch screen without a cursor.

The computing system 600 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C or C++. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 600 may implement the techniques described herein using customized hard-wired logic, one or more ASICs or FPGAs, firmware and/or program logic which in combination with the computer system causes or programs computer system 600 to be a special-purpose machine. According to one embodiment, the techniques herein are performed by computer system 600 in response to processor(s) 604 executing one or more sequences of one or more instructions contained in main memory 606. Such instructions may be read into main memory 606 from another storage medium, such as storage device 610. Execution of the sequences of instructions contained in main memory 606 causes processor(s) 604 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 610. Volatile media includes dynamic memory, such as main memory 606. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 602. Transmission media can also take the form of acoustic or light waves, such as those generated during radio-wave and infra-red data communications.

The computer system 600 also includes a communication interface 618 coupled to bus 602. Network interface 618 provides a two-way data communication coupling to one or more network links that are connected to one or more local networks. For example, communication interface 618 may be an integrated services digital network (ISDN) card, cable modem, satellite modem, or a modem to provide a data communication connection to a corresponding type of telephone line. As another example, network interface 618 may be a local area network (LAN) card to provide a data communication connection to a compatible LAN (or WAN component to communicated with a WAN). Wireless links may also be implemented. In any such implementation, network interface 618 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the world wide packet data communication network now commonly referred to as the "Internet." Local network and Internet both use electrical, electromagnetic or optical signals that carry digital data streams. The signals through the various networks and the signals on network link and through communication interface 618, which carry the digital data to and from computer system 600, are example forms of transmission media.

The computer system 600 can send messages and receive data, including program code, through the network(s), network link and communication interface 618. In the Internet example, a server might transmit a requested code for an application program through the Internet, the ISP, the local network and the communication interface 618.

The received code may be executed by processor 604 as it is received, and/or stored in storage device 610, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, software, or a combination thereof. For example, one or more processors, controllers, ASICs, PLAS, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 600.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A parallel-processing graph-database system for protein-sequence analytics to determine a viable therapeutic for a given condition, comprising:
    at least one processor; and
    memory including instructions that when executed cause the at least one processor to:
        receive, from a user, a query including at least a segment of a protein sequence of the given condition, wherein the query comprises one or more domain specific functions,
        build a sequence database to compare a query sequence of the protein sequence of the given condition with sequences of other known proteins in the sequence database by ingesting data from a file system and converting the data for sequence mapping,
        use the sequence database to determine a similarity of the query sequence with sequences of the other known proteins in the sequence database by performing a first domain specific function of the query to conduct protein similarity analysis,
        perform a second domain specific function of the query to:
            determine respective similarity scores based on the similarity of the sequences of the other known proteins with the query sequence, and
            identify proteins of the sequences of the other known proteins having a similarity score above a determined threshold, and
        identify one or more therapeutics associated with the identified proteins by querying a parallel-processing graph database that comprises potential therapeutics, associated with the identified proteins, that could have an inhibitory effect on the given condition, wherein the query of the parallel-processing graph database includes the identified proteins, and
        return a sorted list of at least a subset of the identified therapeutics associated with the identified proteins, wherein the subset of the identified therapeutics of the sorted list are sorted according the similarity scores of the identified proteins,
        wherein the one or more domain specific functions are executed in parallel.

2. The system of claim 1, wherein identifying the one or more therapeutics comprises identifying drugs in the graph database that are known to have an inhibitory effect on the identified proteins of the other known proteins that have a similarity score above the determined threshold.

3. The system of claim 1, wherein determining a viable therapeutic for the given condition comprises executing a workflow of queries across multiple datasets to generate drug hypotheses of identified drugs.

4. The system of claim 1, wherein querying the graph database comprises searching the graph database to identify therapeutics that have a desired effect on other known proteins having same or similar sequences to the query sequence.

5. The system of claim 1, wherein the converting the data for sequence mapping comprises filtering, grouping and ordering sequences from the data that are executed in parallel with the one or more domain specific functions.

6. The system of claim 1, wherein the data from the file system comprises N-Triple/N-Quad data.

7. The system of claim 1, wherein the determined threshold is based on the query sequence.

8. A computing system for protein-sequence analytics to determine a viable therapeutic for a given condition, comprising:
a hardware processor; and
a machine-readable storage media, coupled to the processor and storing a set of instructions which, when executed by the processor cause the processor to perform operations comprising:
determining a protein sequence of the given condition from a query, wherein the query comprises one or more domain specific functions;
building a sequence database to compare a query sequence of the protein sequence of the given condition with sequences of other known proteins in the sequence database by ingesting data from a file system and converting the data for sequence mapping;
using the sequence database to determine a similarity of the query sequence with sequences of the other known proteins in the sequence database by performing a first domain specific function of the query to conduct protein similarity analysis;
performing a second domain specific function of the query to:
determine respective similarity scores based on the similarity of the sequences of the other known proteins with the query sequence, and
identify proteins of the sequences of the other known proteins having a similarity score above a determined threshold;
querying a graph database based on the similarity of sequences to identify potential therapeutics, associated with the identified proteins, that could have an inhibitory effect on the given condition; and
rebuilding the sequence database according to updated data in the file system and results of querying the graph database,
wherein the one or more domain specific functions are executed in parallel.

9. The computing system of claim 8, wherein identifying the potential therapeutics comprises identifying drugs in the graph database that are known to have an inhibitory effect on the identified proteins of the other known proteins that have a similarity score above the determined threshold.

10. The computing system of claim 8, wherein determining a viable therapeutic for the given condition comprises executing a workflow of queries across multiple datasets to generate drug hypotheses of identified drugs.

11. The computing system of claim 8, wherein the operation of querying the graph database comprises searching the graph database to identify therapeutics that have a desired effect on other known proteins having same or similar sequences to the query sequence.

12. The computing system of claim 8, wherein the converting the data for sequence mapping comprises filtering, grouping and ordering sequences from the data that are executed in parallel with the one or more domain specific functions.

13. The computing system of claim 8, wherein the data from the file system comprises N-Triple/N-Quad data.

14. The computing system of claim 8, wherein the instructions further cause the processor to perform operations comprising:
querying the rebuilt sequence database for a second set of potential therapeutics having a high likelihood of the inhibitory effect on the given condition by having a similarity score above a second determined threshold.

15. A non-transitory computer readable medium storing a set of instructions which, when executed by a computer processing system, causes the computer processing system to perform operations comprising:
determining a protein sequence for a given condition from a query, wherein the query comprises one or more domain specific functions;
building a sequence database to compare a query sequence of the protein sequence of the given condition with sequences of other known proteins in the sequence database, by ingesting data from a file system and converting the data for sequence mapping;
using the sequence database to determine a similarity of the query sequence with sequences of the other known proteins in the sequence database by performing a first domain specific function of the query to conduct protein similarity analysis;
performing a second domain specific function of the query to:
determine respective similarity scores based on the similarity of the sequences of the other known proteins with the query sequence, and
identify proteins of the sequences of the other known proteins having a similarity score above a determined threshold;
querying a graph database based on the similarity of sequences to identify potential therapeutics, associated with the identified proteins, that could have an inhibitory effect on the given condition; and
rebuilding the sequence database according to updated data in the file system and results of querying the graph database,
wherein the one or more domain specific functions are executed in parallel.

16. The non-transitory computer readable medium of claim 15, wherein identifying the potential therapeutics that could have an inhibitory effect on the given condition comprises identifying drugs in the graph database that are known to have an inhibitory effect on the identified proteins of the other known proteins that have a similarity score above the determined threshold.

17. The non-transitory computer readable medium of claim 15, wherein determining a viable therapeutic for the given condition comprises executing a workflow of queries across multiple datasets to generate drug hypotheses of identified drugs.

18. The non-transitory computer readable medium of claim 15, wherein the operation of querying the graph database comprises searching the graph database to identify therapeutics that have a desired effect on other known proteins having same or similar sequences to the query sequence.

19. The non-transitory computer readable medium of claim 15, wherein the converting the data for sequence mapping comprises filtering, grouping and ordering sequences from the data that are executed in parallel with the one or more domain specific functions.

20. The non-transitory computer readable medium of claim 15, wherein the data from the file system comprises N-Triple/N-Quad data.

* * * * *